United States Patent [19]

Sekiguchi et al.

[11] Patent Number: 5,228,973
[45] Date of Patent: Jul. 20, 1993

[54] SAMPLE DILUENT FOR MEASUREMENT WITH ION-SELECTIVE ELECTRODES AND METHOD OF USING THE SAME

[75] Inventors: Mitsuo Sekiguchi, 25-4, Shimizuko, Sakado-shi; Yoshiteru Furuta, Chiba; Daizo Tokinaga, Hachioji, all of Japan

[73] Assignees: Hitachi, Ltd., Tokyo; Mitsuo Sekiguchi, Sakado, both of Japan

[21] Appl. No.: 737,696

[22] Filed: Jul. 30, 1991

[30] Foreign Application Priority Data

Jul. 30, 1990 [JP] Japan .................................. 2-199296

[51] Int. Cl.⁵ .............................................. G01N 27/26
[52] U.S. Cl. .................................... 204/416; 204/418; 204/419; 204/433; 204/435; 204/153.21
[58] Field of Search ............... 204/416, 417, 418, 419, 204/433, 435, 153.21

[56] References Cited

U.S. PATENT DOCUMENTS 4,409,088 10/1983 Kanno et al. .................... 204/418
4,619,739 10/1986 Kanno et al. .................... 204/416

FOREIGN PATENT DOCUMENTS 60-228951 6/1985 Japan .
61-240156 11/1986 Japan .
61-290353 12/1986 Japan .
2-16441 2/1990 Japan .

*Primary Examiner*—T. Tung
*Assistant Examiner*—Bruce F. Bell
*Attorney, Agent, or Firm*—Fay, Sharpe, Beall, Fagan, Minnich & McKee

[57] ABSTRACT

A body fluid sample is diluted with a diluent which comprises an aqueous solution containing bis(2-hydroxyethyl)-iminotris(hydroxymethyl)methane and boric acid to obtain a diluted body fluid sample, and the ion concentration in the diluted body fluid sample is determined with ion-selective electrodes, whereby the variation width of pH in the diluted body fluid sample can be held down to a narrow range. As a result the determination can be made without exerting adverse effects on the ion-selective electrodes, and errors in determination can be markedly reduced as compared with cases where the conventional diluents are used.

9 Claims, 1 Drawing Sheet

SAMPLE DILUENT FOR MEASUREMENT WITH ION-SELECTIVE ELECTRODES AND METHOD OF USING THE SAME

BACKGROUND OF THE INVENTION

1. Field of the Invention

The present invention relates to a sample diluent for use in determination of ion concentration using ion-selective electrodes, and to a method of using the same. In particular, it relates to a diluent suitable for use in determining ion concentration in body fluids such as blood, urine, etc. with ion-selective electrodes, and to a method of determining ion concentration which uses the diluent.

2. Description of the Related Art

In the analysis of body fluids such as blood, urine, etc. in laboratories of hospitals or such, a vast number of analyses are made for sodium cation, potassium cation and chlorine anion. For the determination of these ions, flame analysis and coulometric titration long have been used. However, in recent years, the ion-selective electrode method has come to be in wide use. In using ion-selective electrodes, the sample is usually diluted to an appropriately low concentration with a diluent prior to the determination. The dilution is usually necessary for decreasing the amount of the sample such as blood or for adjusting the concentration of the constituents to be subjected to the measurement to the range within which the electrodes fully exhibit their capacity. The factor of dilution is generally from ten-fold to several ten-fold, although it may vary depending on the kind of autoanalyzer to be used, or for other reasons.

Due consideration has not been given to the hydrogen ion concentration (namely, pH) of the samples diluted with the conventional, commercially available diluents. Therefore, the pH of the diluted sample to be analyzed often varies from sample to sample. Particularly, when urine which originally has a wide variation of pH among different samples is used as a sample, the pH of the diluted sample to be analyzed varies widely, leading to a large error in the results of ion concentration determination. Accordingly, in order to enhance the accuracy of ion concentration determination, the improvement of diluents in this respect has been eagerly desired.

JP-A-60-228951 and JP-A-61-290353 disclose the use of a mixture of tris(hydroxymethyl)aminomethane and boric acid as a sample diluent in determination of ion concentration using ion-selective electrodes.

SUMMARY OF THE INVENTION

An object of the present invention is to provide a sample diluent which can adjust and keep the pH of a body fluid sample after dilution within a certain narrow range and, at the same time, exerts no adverse effect on ion-selective electrodes.

Another object of the present invention is to provide a method of determination of ion concentration in body fluids which method uses the sample diluent of a novel composition.

In order to achieve the above objects, it is necessary to increase the pH-buffering capacity of diluents. However, not all the diluents with a high buffering capacity are always satisfactory; rather, there are many other requirements that the diluents for use in the ion-selective electrode method must satisfy. First, diluents containing the same ion species as that to be determined are basically unusable since the ion itself will disturb the determination. Moreover, although there have been known various aqueous solutions which have a high pH-buffering capacity, which are generally called buffer solutions, many of them ,(e.g,. phosphate buffers, borate buffers and Tris hydrochloride buffers) contain at least one of sodium cations, potassium cations, chlorine anions and other ions, so that they cannot be used when these ions are intended to be determined. Further, even when buffer solutions contain no ion species to be determined, many of them exert adverse effect on one or both of the ion-selective electrodes in respect to such electrode characteristics as slope sensitivity and life. Such buffer solutions also are not suitable for use. Additionally, the storage stability and cost of diluents themselves are also important factors.

The present inventors have made extensive study, in due consideration of the above requirements, to find a diluent which has a sufficiently high pH-buffering capacity even for samples to be analysed having a wide variation of pH such as urine, and as a result have accomplished the present invention.

According to the present invention, there is provided a sample diluent for ion concentration determination using ion-selective electrodes, which diluent comprises an aqueous solution containing bis(2-hydroxyethyl)-iminotris(hydroxymethyl)methane and boric acid, and a method for determination of ion concentration in body fluids which comprises the steps of (i) diluting a body fluid sample with a diluent comprising an aqueous solution containing bis(2-hydroxyethyl)-iminotris-(hydroxymethyl)methane and boric acid to obtain a diluted body fluid sample, and (ii) determining the concentration of ions in the diluted body fluid sample with ion-selective electrodes.

DESCRIPTION OF THE PREFERRED EMBODIMENTS

Figure 1:
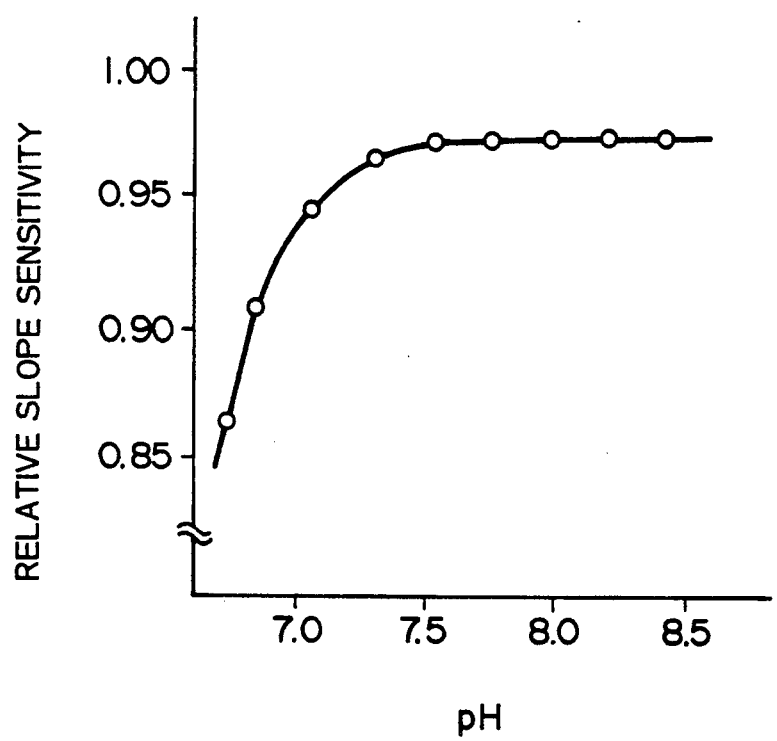
FIG. 1 presents a curve of the relative slope sensitivity of ion-selective electrodes when the diluent of the present invention is used vs. the pH of the diluent used for determination.

The sample diluent for ion concentration determination using ion-selective electrodes according to the present invention comprises an aqueous solution containing bis(2-hydroxyethyl)-iminotris(hydroxymethyl)methane (hereinfter bis-tris) and boric acid. The diluent is usually used after being adjusted to an approximately neutral constant pH. The concentration of bis-tris in the diluent is not critical; however, it is preferably adjusted to a concentration within the range of from 5 mmol/l to 150 mmol/l.

According to the diluent of the present invention, the pH-buffering capacity of diluent used in determining ion concentration in body fluid samples with ion-selective electrodes is surprisingly enhanced.

Bis-tris is generally named "bis(2-hydroxy-ethyl)-iminotris(hydroxymethyl)methane". The combination of bis-tris and boric acid exhibits a high pH-buffering capacity in the vicinity of neutrality. Bis-tris is commercially available from Wako Pure Chemical Industries, Ltd. The diluent of the present invention exerts no adverse effect on the characteristic properties of any ion-selective electrodes for use in determination of sodium cation, potassium cation or chlorine anion, which electrodes are provided with a membrane containing an ion-responsive material. The diluent can keep the pH of samples of blood or urine after dilution in an intended narrow range even when the original samples differ considerably in pH.

Body fluid samples are usually diluted 10- to 50-fold with the diluent of the present invention and then contacted with ion-selective electrodes to determine ion concentration in the samples. The pH of the diluent itself is adjusted beforehand to a predetermined value in the pH range of usually 6.80–8.40, preferably 7.30–8.40. By use of the diluent of the present invention, the pH of body fluid samples after dilution can be kept between 6.70 and 8.45, and the width of variation of pH can be held down to 0.25 or less in terms of standard deviation for 10–20 samples for the same sample species (i.e. between plural blood samples or between plural urine samples) at the same dilution.

Table 1 shows the mean values of pH of urine sample solutions after dilution and variation widths thereof expressed in terms of standard deviation (indicated in parenthesis in Table 1) in the case where a diluent comprising bis-tris and boric acid adjusted to a pH of 9.65 used, and the concentration of bis-tris and the dilution were varied. The number of the original urine samples was 20. The urine samples had pH values distributed between 4.95 and 9.01 with a mean value of 6.70 and a standard deviation of 1.62.

The lower limit of dilution in the practically acceptable range is about 10-fold. At 10-fold dilution, it can be seen from Table 1 that the pH variation width of diluted samples can be kept within the intended range so long as the bis-tris concentration is 5 mmol/l or more.

TABLE 1

| Bis-tris concentration | pH of Urine after Dilution | | |
|---|---|---|---|
| | Dilution | | |
| | 10-fold | 20-fold | 40-fold |
| 2.5 mmol/l | 6.77 | 6.80 | 6.83 |
| | (0.44) | (0.21) | (0.15) |
| 5 mmol/l | 6.81 | 6.83 | 6.83 |
| | (0.22) | (0.18) | (0.16) |
| 10 mmol/l | 6.85 | 6.88 | 6.92 |
| | (0.12) | (0.14) | (0.09) |
| 20 mmol/l | 6.88 | 6.92 | 6.93 |
| | (0.15) | (0.08) | (0.08) |
| 30 mmol/l | 6.92 | 6.93 | 6.94 |
| | (0.12) | (0.09) | (0.08) |
| 40 mmol/l | 6.93 | 6.94 | 6.95 |
| | (0.11) | (0.08) | (0.08) |

On the other hand, from the viewpoint of electrode life in using urine or blood as the sample, the pH of the diluent comprising bis-tris and boric acid is preferably 7.30 or more. The higher the pH of the diluent, the higher the concentration of bis-tris necessary for attaining a sufficient pH-buffering capacity. However, when the bis-tris concentration exceeds 150 mmol/l, the pH-buffering capacity for urine and blood does not change appreciably any more, so that a concentration higher than 150 mmol/l is not advantageous when the cost of the reagent is taken into consideration.

Further, increasing the bis-tris concentration necessitates increasing the boric acid concentration to keep the pH constant. Such increased boric acid concentration is not preferable since it may interfere with the determination of chlorine anion.

For storage stability, the diluent of the present invention may contain one or more known stabilizers. Of the stabilizers, formalin is preferable.

The ion-selective electrodes used in the following experiments are ion-selective electrodes provided with a polymer membrane incorporated with an ion-responsive substance. Specific examples of the ion-responsive substances are, respectively, crown ether for sodium cation determination, valinomycin for potassium cation determination, and a quaternary ammonium salt for chlorine anion determination. These three kinds of ion-selective electrodes are arranged in series in a flow cell along with a reference electrode, and a sample diluted with a diluent is introduced into the flow cell. When columnar ion-selective electrodes are used, it may be possible to insert three kinds of such ion-selective electrodes and a reference electrode into a measuring cell and then introduce a sample and a diluent into the measuring cell. As ion-selective electrodes other than those described above, for example, a semiconductor electrochemical sensor, etc., may also be used.

The present invention will be described in detail below with reference to Examples.

EXAMPLE 1

Into a 10 mmol/l aqueous bis-tris solution was added, with thorough stirring, powdery boric acid in small portions to prepare a solution adjusted to pH 6.91. With the resulting solution used as the diluent, human serum and urine were diluted 17-fold to obtain diluted samples, and their pHs were determined. The results obtained are shown in Table 2. The number of samples was 10 for each case. For reference, a commercially available sample diluent for ion-selective electrodes was used to obtain 17-fold diluted samples and to determine their pHs. The results thus obtained are shown as reference in Table 2.

TABLE 2

| pH Mean Value and Standard Deviation | | | | |
|---|---|---|---|---|
| | Serum | | Urine | |
| | Mean value | Standard deviation | Mean value | Standard deviation |
| Before dilution | 8.50 | 0.17 | 6.72 | 1.58 |
| After dilution | 7.06 | 0.02 | 6.83 | 0.20 |
| Conventional diluent (Reference) | 7.32 | 0.04 | 6.45 | 0.77 |

The diluent of the present invention made the width of pH variation of diluted sample solutions narrower than does the conventional diluent. Even when urine was used as the sample, the standard deviation was as small as 0.20. Thus, the diluent of the present invention showed a remarkable pH-buffering capacity.

The influence of the diluent of Example 1 exerted on the performance of electrodes was examined by using commercially available sodium cation-selective electrodes, potassium cation-selective electrodes and chlorine anion-selective electrodes. In detail, human pooled serum and pooled urine were diluted 17-fold with the diluent of the present invention, then respective electrode paths were immersed in the resulting diluted samples, and the change in slope sensitivity with the passage of time was examined. As a result, it was found that in all cases and even in an immersion of as long as 120 hours, the electrodes maintained practically usable slopes and thus the diluent of the present invention is proved to permit the use of electrodes for a long period of time without damaging their performance.

Thus, the use of the diluent of the present invention narrows the variation width of the pH of sample solutions after dilution without damaging the performance of ion-selective electrodes.

EXAMPLE 2

Into a 20 mmol/l aqueous bis-tris solution was added, with thorough stirring, powdery boric acid in small portions to prepare a solution adjusted to pH 6.91. The resulting solution was charged as a diluent for electrolytes into a Hitachi Model 7150 autoanalyzer, and the concentrations of the sodium, cation, potassium cation and chlorine anion were analyzed for 36 urine samples. The autoanalyzer dilutes samples 31-fold with a diluent and analyzes these three kinds of ions by means of ion-selective electrodes. For comparison, the same 36 samples were analyzed by standard methods. The standard method referred to herein is the flame analysis for sodium and potassium cations and the coulometric titration for the chlorine anion.

Table 3 shows the correlation coefficients with the standard method and the error variance, for respective ion species. The error variance is defined by the following equation and signifies that the smaller the values of error variance, the more accurate the values obtained by means of ion-selective electrodes are.

$$\text{Error variation} = \sqrt{(\Sigma(y - y')^2 - b^2\Sigma(x - x')^2/(n - 2)}$$

wherein
- x: measured value by standard method,
- y: measured value by ion-selective electrode method,
- x': mean of measured values by standard method,
- y': mean of measured values by ion-selective electrode method
- b: slope of regression line,
- n: number of samples.

For comparison, a commercially available diluent was charged into the Hitachi Model 7150 autoanalyzer, and analysis was made with the same 36 samples as above. The results thus obtained are shown as reference values in Table 3.

TABLE 3

|  |  | Correlation coefficient | Error variance |
|---|---|---|---|
| Sodium cation | Diluent of the present invention | 0.9988 | 2.79 |
|  | Reference | 0.9986 | 3.09 |
| Potassium cation | Diluent of the present invention | 0.9977 | 1.99 |
|  | Reference | 0.9931 | 3.69 |
| Chlorine anion | Diluent of the present invention | 0.9972 | 4.46 |
|  | Reference | 0.9948 | 5.92 |

It was revealed that with any of the ion-selective electrodes, the use of the diluent of the present invention resulted in better values both in correlation coefficient and in error variance, showing that the measured values were more accurate, as compared with the use of the commercially available diluent.

EXAMPLE 3

A diluent (pH 7.58) comprising 50 mmol/l of bis-tris, 20 mmol/l of boric acid and 0.1% of formaldehyde was charged into a Hitachi Model 7150 autoanalyzer, and sera were analyzed. The results of determination were satisfactorily accurate as in Examples 1 and 2. Also it was revealed that the diluent of the present invention has an additional advantage; that is, the diluent of the present invention permits the ion-selective electrodes to keep their slope sensitivity unchanged during the analysis of a large number of specimens that cannot be achieved by the use of the commercially available diluent. Specifically, the commercially available diluent reduced the slope sensitivity of potassium cation-selective electrodes by 10-15% of the initial slope sensitivity after 10,000 specimens had been analyzed, whereas the diluent of the present invention reduced the slope sensitivity by only 3% or less under the same conditions.

The above-mentioned advantage of prolonging the life of electrodes was further examined by varying the pH and concentrations of bis-tris and boric acid in the diluents of the present invention. FIG. 1 shows the results of the tests in which the influence of the diluent to chlorine anion-selective electrodes was examined. The numbers on the ordinate indicate the relative slope sensitivity of the chlorine anion-selective electrodes after analysis of 10,000 serum specimens based on the initial slope sensitivity. It is signified that the higher the value is, the higher is the effect of prolonging the life of the electrodes. It is revealed that the use of a diluent of pH 6.80 or higher permits the electrodes to maintain their slope sensitivity at 90% or more of the initial value, and the use of a diluent of pH 7.30 or higher permits the electrodes to maintain their slope sensitivity at 95% or more of the initial value. In summary, the effect of prolonging the life of electrodes is marked when a diluent of pH 6.90 or more, particularly pH 7.30 or more, is used.

It is also revealed that diluents with a pH higher than 8.40 comprising bis-tris and boric acid are of no practical use because such diluents have a high boric acid concentration, the boric acid ion acts as an interfering ion particularly against chlorine anion-selective electrodes, and it deteriorates the accuracy of the chlorine anion-selective electrodes. Diluents of a pH higher than 8.40 are not preferable also from an economical viewpoint because the amount of bis-tris used therein is largely excessive in comparison with its pH-buffering capacity.

Thus, the present invention has the advantage of preventing the reduction of the slope sensitivity of ion-selective electrodes. The advantage is particularly marked with diluents having a pH higher than 7.30.

EXAMPLE 4

The diluent of the present invention (pH 7.58) comprising 50 mmol/l of bis-tris, 20 mmol/l of boric acid and 0.1% formaldehyde was charged into a Hitachi Model 7150 autoanalyzer, determinations were carried out 20 times with the same single serum sample. It was found that the reproducibility of the results of chlorine anion concentration determination was 0.16% in terms of CV value. For the sake of comparison, a diluent (pH 7.58) comprising 50 mmol/l of tris(hydroxymethyl)aminomethane, boric acid and 0.1% formaldehyde was prepared, and 20 times of repeated determinations were carried out with the same serum sample as used above, to find a CV value of 0.45%. Thus, the diluent of the present invention has an advantage of enhancing the reliability of the results of determination.

As described above, according to the present invention, the pH of the sample solution to be analyzed can be kept constant and the accuracy of the results of determination using ion-selective electrodes can be enhanced irrespective of whether the sample is blood, urine or the like. In order that diagnoses are made more correctly, increasingly higher accuracy of the results of determination is required for clinical chemical tests in future. The present invention meets such a requirement.

What is claimed is:

1. A diluent for samples for determination of ion concentration using ion-selective electrodes which comprises an aqueous solution containing bis(2-hydroxyethyl)-iminotris(hydroxymethyl)methane and boric acid.

2. The diluent of claim 1, wherein the concentration of bis(2-hydroxyethyl)-iminotris(hydroxymethyl)methane in the aqueous solution falls within the range of from 5 mmol/l to 150 mmol/l.

3. The diluent of claim 1, wherein the diluent has a pH falling within the range of from 6.80 to 8.40.

4. The diluent of claim 1, wherein the diluent has a pH falling within the range of from 7.30 to 8.40.

5. The diluent of claim 1, wherein the diluent is suited for use in determination of the concentration of at least one ion selected from the group consisting of sodium cation, potassium cation and chlorine anion.

6. A method for determination of ion concentration in body fluids which comprises the steps of:
   (i) diluting a body fluid sample with a diluent comprising an aqueous solution containing bis(2-hydroxyethyl)-iminotris(hydroxymethyl)methane and boric acid to obtain a diluted body fluid sample, and
   (ii) determining the concentration of an ion in the diluted body fluid sample with ion-selective electrodes.

7. The method of claim 6, wherein the step (ii) includes the step of providing the ion-selective electrodes with a polymer membrane incorporated with an ion-responsive substance.

8. The method of claim 6, wherein the step (ii) includes the step of selecting as the ion-selective electrode at least one electrode selected from the group consisting of sodium cation-selective electrodes, potassium cation-selective electrodes and chlorine cation-selective electrodes.

9. The method of claim 6, wherein the step (i) includes the step of adjusting the pH of the diluted body fluid sample to a pH between 6.70 and 8.45.

* * * * *